United States Patent [19]

Morel et al.

[11] Patent Number: 4,818,683
[45] Date of Patent: Apr. 4, 1989

[54] IMMUNOASSAY FOR MONOAMINES

[75] Inventors: Anne Morel; Michel Delaage, both of Marseille, France

[73] Assignee: Immunotech, Paris, France

[21] Appl. No.: 83,899

[22] Filed: Aug. 6, 1987

Related U.S. Application Data

[63] Continuation of Ser. No. 719,873, Apr. 4, 1985, abandoned.

[30] Foreign Application Priority Data

Apr. 10, 1984 [FR] France .................. 84 05783

[51] Int. Cl.[4] .................. G01N 33/53; G01N 33/536; C07K 17/02
[52] U.S. Cl. .................. 435/7; 435/188; 435/810; 436/543; 436/544; 436/545; 436/546; 436/547; 436/548; 436/518; 436/536; 436/808; 436/815; 436/822; 436/823; 530/404; 530/405; 530/406; 530/807; 530/362
[58] Field of Search .................. 424/85, 88, 94; 530/807, 403, 404, 405, 406, 362; 435/7, 188, 810; 436/543–548, 518, 536, 808, 815, 822, 823

[56] References Cited

U.S. PATENT DOCUMENTS

| | | | |
|---|---|---|---|
| 2,372,066 | 12/1940 | Fell | 424/88 |
| 3,975,342 | 8/1976 | Gross | 260/112 R |
| 4,241,177 | 12/1980 | Singh et al. | 260/112 R |
| 4,299,813 | 11/1981 | Snyder | 436/504 |
| 4,342,780 | 2/1982 | Bey et al. | 514/563 |
| 4,495,281 | 1/1985 | Buckler et al. | 435/7 |
| 4,506,009 | 3/1985 | Lenhoff | 435/7 |

FOREIGN PATENT DOCUMENTS

| | | | |
|---|---|---|---|
| 0116095 | 5/1941 | Australia . | |
| 8504331 | 7/1986 | Australia . | |
| 8604420 | 7/1986 | Australia . | |
| 0006792 | 1/1980 | European Pat. Off. . | |
| 0208953 | 1/1987 | European Pat. Off. | 435/68 |
| 1341375 | 12/1973 | United Kingdom . | |

OTHER PUBLICATIONS

Delaage et al., *J. Physiol*, 77, 1981, pp. 339–347.
Mita et al., *Agents and Artivi*, 6/1984, vol. 14, pp. 574–579.
Panula et al., *PNAS* 81, 1984, pp. 2572–2576.
Burtin–Laborde, CA, vol. 74, 1971, #123114a.
Bieganski et al., CA vol 104, 1986, #144491z.

Primary Examiner—Howard E. Schain
Assistant Examiner—Garnette D. Draper
Attorney, Agent, or Firm—Browdy & Neimark

[57] ABSTRACT

The invention relates to a method of immunoassay for monoamines (molecules having a primary or secondary amine function) comprising chemical quantitative conversion of such amines into derivatives of higher molecular weight, which thereafter are brought into competition with radioactive analogous, or analogous carrying a tracer, for fixation to an antibody capable of recognizing all of them.

10 Claims, 1 Drawing Sheet

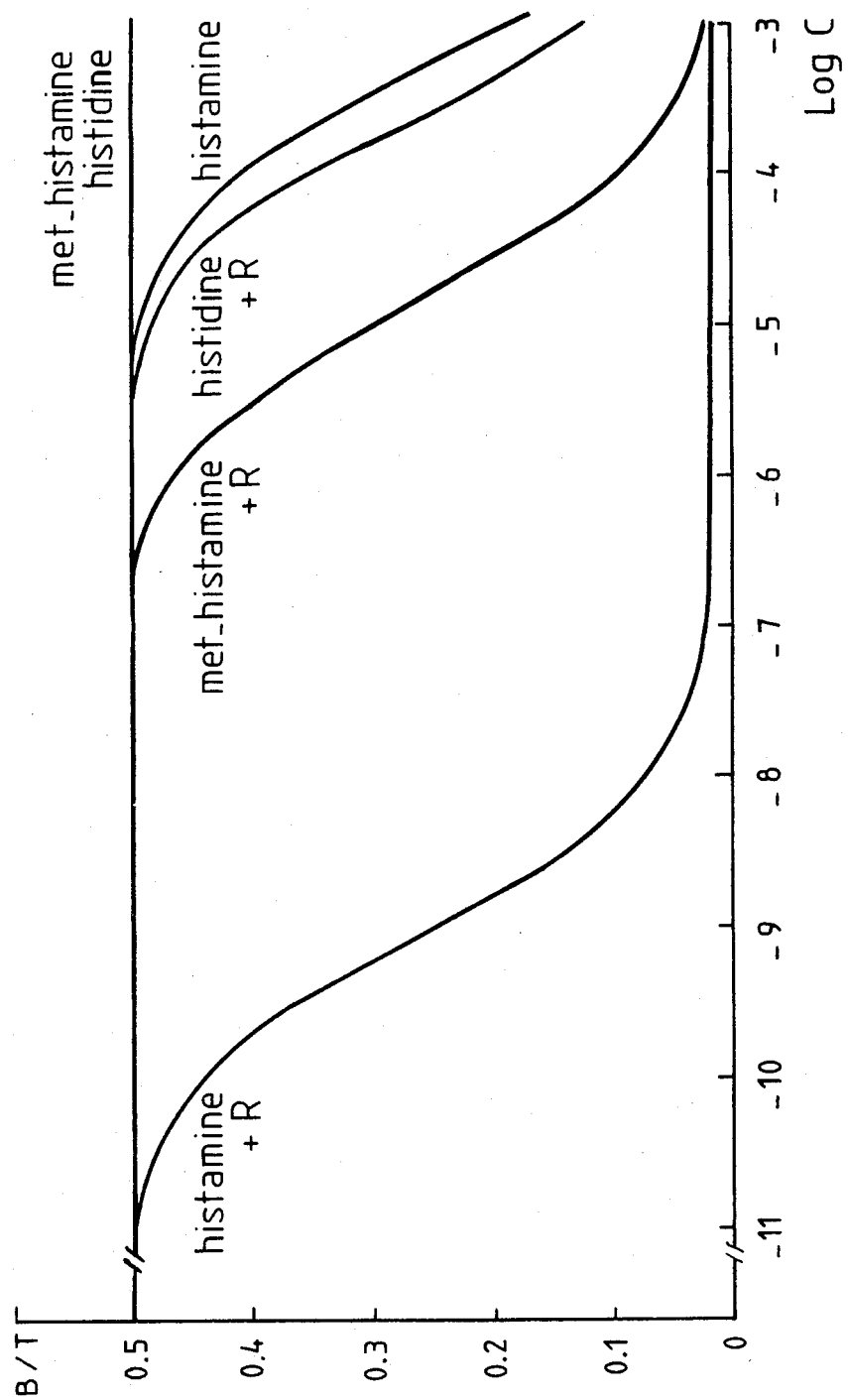

IMMUNOASSAY FOR MONOAMINES

This application is a continuation of application Ser. No. 719,873, filed Apr. 4, 1985, now abandoned.

A biological monoamine is an amine resulting from the decarboxylation of an amino-acid, accompanied or not by oxidation of the residue. Such amines are found in the nervous system where they act as neuro-transmitters. Thus, there are known:

derivatives of tryptophan or indolamines, tryptamine, 5-hydroxytryptamine (serotonin), 5-methoxy-tryptamine;

derivatives of tyrosine, tyramine and catecholamines such as adrenaline, noradrenaline, dopamine, and so on;

the derivative of histidine, histamine; and the derivative of glutamic acid, gamma amino-butyric acid (GABA).

Chemically, the term monoamine includes many more molecules having the general formula R—$NH_2$, where R is a substituted or unsubstituted hydrocarbon radical and includes natural amino-acids with no special reference to the nervous system.

Generally, the monoamines are assayed, after chromatography, by coupling with a chromophore such as ninhydrin, causing a color reaction, or a dansyl residue, causing a fluorescence reaction. Less often, the assay employs the coupling of the monoamine radical moiety, for example, histamine with orthophtalaldehyde. Indolamines and catecholamines are assayed by polarographic methods (see "Methods in Enzymology", vol. XVII, H. Tabor and C. Tabor Eds. Academic Press, N.Y., 1971; Mefford I. N. and Barchas J. D., *J. Chromatogr.* 181, 187–193 (1980)).

All of these methods require extraction and/or chromatography to achieve specificity. Their sensitivity (scarcely ever beneath 10 ng) limits their use for biological analysis on samples of necessarily limited volume.

Moreover, enzymes may be prepared for radioenzymatic assays, such as, for example, methyltransferase in the case of histamine (C. Bruce, W. H. Taylor and A. Westwood (1979) "Annals of Clinical Biochemistry" 16, 259–264). These methods have no industrial value.

Furthermore, it has been attempted to apply to monoamines the general principle of immunoassays of small molecules in which the compound to be assayed competes with its radioactive analogs or any other type of tracer for fixation to an antibody able to recognize both of them.

Molecules of low molecular mass, such as histamine or the other monoamines, do not allow such processing, since they do not exhibit sufficiently strong interactions with antibodies.

One author of this invention (M. A. Delaage) has published a radioimmunological assay method for serotonin wherein serotonin is reacted with succinic anhydride to increase the immuno-reactivity of the serotonin molecule (*J. Physiol.*, Paris, 1981, 77, 339–347) and a similar method wherein serotonin is reacted with acetic anhydride (*Journal of Neurochemistry*, 1982, 39, 1271–1277). In each case, the reaction product competes with its radioactive analog for fixation to the suitable antibody.

However, these methods are not satisfactory for very small molecules (MW less than 150) since the contribution of the succinate group, and to a greater degree acetate, increases binding potency by only 1000 fold or less. This increase is insufficient for conferring suitable affinity upon the molecule to its antibody.

This invention overcomes these disadvantages by providing a novel chemical conversion of the monoamine to be assayed by means of a novel reagent. This novel conversion confers upon the monoamine an affinity gain on the order of 500,000 toward the antibody produced against the modified molecule coupled to a carrier protein.

Under these conditions, immunoassays of the monoamines may obtain the same level of sensitivity as obtained by immunoassays of molecules of higher molecular weight, such as steroids and peptides. The process according to this invention is particularly applicable to very small monoamines of a molecular weight below 150, such as histamine.

The monoamine immunoassay according to the present invention employs three reagents:

1. An acylation reagent (I) which reacts with the primary amine function, transforming it into a substituted amide group as follows:

$$X-NH_2 + R-CO-R' \longrightarrow$$

monoamine (I)

$$X-NH-CO-R + R'-H$$

Modified monoamine (IV)

where X is the monoamine residue, such as for example:

X = (imidazole)—$CH_2$—$CH_2$—   for histamine

X = (3,4-dihydroxyphenyl)—$CH_2$—$CH_2$—   for dopamine or the analogously structured residues of other amines such as serotonin or other indolamine, the catecholamines (adrenaline, noradrenaline) or an amino acid such as gamma-amino-butyric acid, glutamate and analogs; and (I) is the acylation reagent in which:

R is $NH_2$—CO—$CH_2$—NH—CO—$CH_2$—$CH_2$—;

R' represents a leaving group such as:

—O—N(CO—$CH_2$—$CH_2$—CO) (N—hydroxysuccinimide)

or —Cl (or more generally halogen)

or —O—CO—R" (R"=hydrocarbon radical)

or —S—R"

or HO—(phenyl), etc;

the formed product (IV) being either an amide if R is an alkyl residue or a carbamate if R is an alkoxy radical;

2. A tracer (II) having the general formula:

$$X-NH-CO-R_1 \quad (II)$$

where X has the above meaning and $R_1$ is a radical selected so that the tracer (II) competes with the modified monoamine (IV) for binding to the same antibody, the radical being coupled to the amine by the acylation reagent (I). $R_1$ may contain radioactive iodinated tyrosine residue coupled to an amide or ester (according to an advantageous modification, the tracer may be enzymatic, that is, the radical X—N-H—CO—$R_1$ is coupled to a lysine residue of an enzyme conventionally used for this purpose; according to another modification, the tracer may be fluorescent); and 3. A monoclonal or polyclonal antibody (III) able to to recognize the modified monoamine (IV) and the tracer; antibody (III) must be produced against a conjugate (V) or (VI) built from the amine X—$NH_2$ or from its parent amino acid $NH_2$—$X_1$—COOH, where $X_1$=X—H, (V) being X—NH—CO—$R_2$—CO—NH—protein, where $R_2$ is a residue related to R by the relationship:

$$-R = R_2-CO-NH_2, \text{ and}$$

(VI) being R—CO—NH—X—CO—NH—protein.

Once the three reagents, i.e. (I) the conversion reagent; (II) the tracer; and (III) the antibody have been obtained, the assay is carried out as follows:

1. The sample to be assayed (a few hundred microliters) is admixed with the acylation reagent and a suitable buffer (neutral or slightly alkaline), to convert all of the amines functions into (IV).

2. The so converted product is coincubated with the tracer (II) and calibrated amounts of antibody (III).

3. After incubation, the antigen-antibody complexes are isolated and the radioactivity bound to the antibody is determined. The greater the quantity of X—N-H—CO—R (IV) molecules in comparison to tracer molecules, the lower is the bound radioactivity. The quantity of X—$NH_2$ present at the beginning is deduced by comparison with a standard curve.

An analogous process is carried out when a non-radioactive tracer is used, except that $R_1$ is bound to the appropriate tag (e.g., fluorescent or enzymatic) and the results of the competitive assay are determined by measuring a property of that tag, e.g., fluorescence or enzymatic activity, rather than radioactivity.

A particularly suitable acylation reagent (I) is the novel compound having the general formula:

$$NH_2-CO-CH_2-NH-CO-CH_2-CH_2-CO-O-N\begin{matrix}CO-CH_2\\|\\CO-CH_2\end{matrix} \quad (I)$$

(I) = N-hydroxysuccinimide ester succinyl glycinamide, (I) can be obtained by succinylation of the gylcinamide by reacting one equivalent of succinic anhydride with 5 milliequivalents of glycinamide in the presence of 5 milliequivalents of triethylamine, each reagent being dissolved in dimethylformamide. The succinylglycinamide is separated from the excess of glycinamide on an ion-exchange resin of the QAE Sephadex $A_{25}$ type, which is a quaternary ammonium cationic ion exchange resin produced by Pharmacia, at neutral pH. Succinyl-glycinamide is then eluted at acid pH. The fractions containing succinylglycinamide are pooled and then lyophilized.

The following steps require anhydrous dimethylformamide. Five milliequivalents of succinyl-glycinamide are activated 5 mn at 4° C. by 5 milliequivalents of ethylchloroformate, then coupled with N-hydroxysuccinimide (7 milliequivalents). The activated product is solidified as a precipitate by addition of dioxane. The resulting precipitate is rinsed with ether, then lyophilized.

The final product is a white powder soluble in dimethylformamide and in water, where it quickly hydrolyzes, and is insoluble in most organic solvents.

Its melting point is 108°–110° C.

Its molecular weight is 307.7.

The following example is given merely by way of illustration only and not in a limiting manner.

EXAMPLE

Radioactive immunoassay for histamine after NOH-succinimide-ester-succinyl-glycinamide conversion of histamine The acylation reagent (I) was the one previously described:

$$NH_2-CO-CH_2-NH-CO-CH_2-CH_2-CO-O-N\begin{matrix}CO-CH_2\\|\\CO-CH_2\end{matrix}$$

(I) = NOH-succinimide-ester-glycinamide.

Histamine is directly acylated by (I) in slightly alkaline medium (pH = 8) into:

$$\underset{HN\diagdown N}{\boxed{\phantom{xx}}}-CH_2-CH_2-NH-CO-CH_2-CH_2-CO-NH-CH_2-CO-NH_2 \quad (IV)$$

(IV) = histamine-succinyl-glycinamide.

The radioactively labeled tracer was obtained by fixation of succinyl to the amine function, then coupling it to glycyltyrosinamide, which was iodinated to form (IIa):

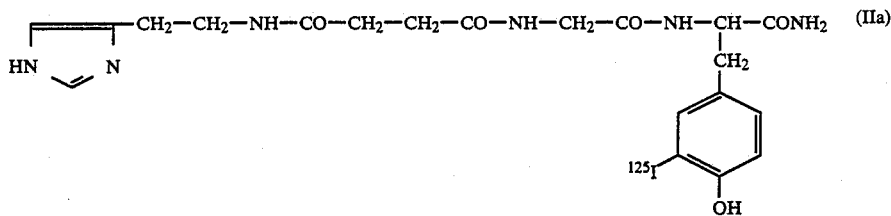

The carboxylated form of (IIa), (IIb) may also be used:

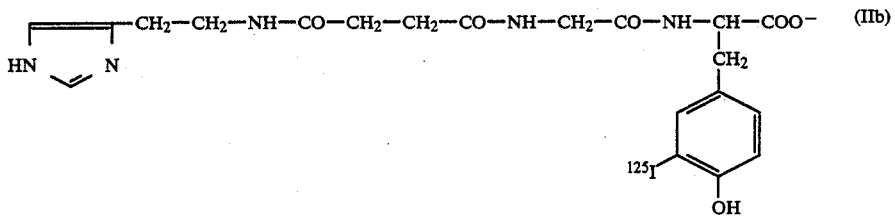

A modification of the tracer may consist of the succinyl-histamine coupled to an enzyme.

The corresponding antibodies (III) were obtained after injection into an animal of the immunogenic derivative (V) prepared as follows:

After fixation of the succinyl link to the amine function of histamine, the succinyl-histamine was coupled to the glycylalbumin (any other modified or unmodified protein carrier is also suitable).

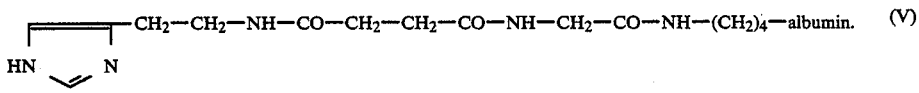

Monoclonal antibodies were obtained after injecting the immunogenic derivative (V) into mice, then fusing the immune mouse splenocytes with mouse myeloma cells (lineages X63) in the presence of PEG 4000 as described by Galfre et al. (Nature, 1977, 266, 550–552).

Several suitable monoclonal antibodies were selected for their ability to bind the iodinated derivative (II). The appropriate clone 679 AM was selected for its affinity and selectivity toward the acylated histamine (higher discrimination with respect to histamine analogs). Antibodies produced in ascitic fluid were purified on protein A Sepharose, then coated on the assay tube according to the method described in Immunotech French Patent Application No. 83 05617.

The attached FIGURE shows the displacement of the radio-labeled derivative by histamine or its metabolites before and after acylation. The FIGURE illustrates the increased sensitivity which resulted from the acylation and the selectivity of the assay. After acylation, histamine is $5(10^5)$ times better recognized. Moreover, t-methyl-histamine, a product of degradation of histamine is $10^4$ times less recognized, even after acylation. Acylated histamine is less recognized than is native histamine.

From the above, one skilled in the art will observe that simple immunoassays for monoamines are made available by the present invention. The present invention also permits the production of assay packages containing ready-for-use reagents for carrying out the process of the invention. It will be understood that this invention was described in a purely explanatory manner and not at all in a limiting manner and that any useful modification can be made to the invention without departing from its scope.

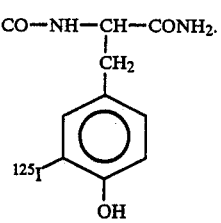

We claim:

1. A method for the immunoassay of a primary or secondary monoamine present in a biological sample, comprising the steps of:

acylating said monoamine while present in said biological sample by an acylation reagent (I) of the formula:

$$R-CO-R'$$

in which
R is $NH_2-CO-CH_2-NH-CO-CH_2-CH_2-$ and R' represents a leaving group selected from the group consisting of an N-hydroxysuccinimide group, halogen, $-O-CO-R''$ and $-S-R''$, wherein R'' is a hydrocarbon radical or $OH-C_6H_5-$ to form an acylated monoamine coupling said acylated monoamine to a macromolecular carrier to form an immunogenic complex;

producing an antibody against said immunogenic complex;

selecting a tracer having the formula: $X-NH-CO-R_1$, wherein $R_1$ is a radical selected so that said tracer binds to said antibody competively with respect to said acylated monoamine, that is coupled to (1) a radioactive iodonated tyrosine residue or (2) an enzyme residue and X is the residue of said monoamine;

performing a competitive binding assay of said biological sample comprising said acylated monoamine against said tracer for said antibody.

2. The method of claim 1, wherein said immonogenic complex is a conjugate of the structure $X-NH-CO-R_2-CO-NH-$protein wherein $R_2$ is related to the acylation reagent by the relationship:

$$-R = -R_2-CO-NH_2.$$

3. A method according to claim 1, wherein said acylating reagent has the formula:

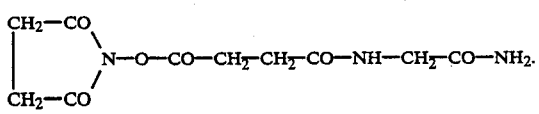

4. The method of claim 1, wherein —R₁ has the formula:

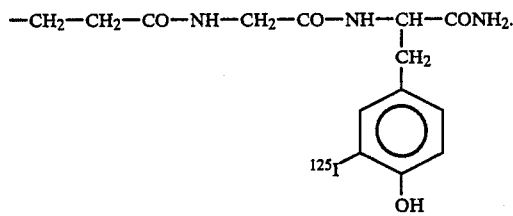

5. A method according to claim 4, wherein said tracer is obtained by reaction of the monoamine with a reagent having the following formula:

to produce:

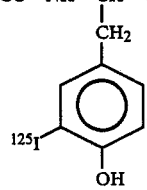

X—NHCO—CH₂CH₂CO—NH—CH₂—CO—NH—CH—CONH₂.

6. An immunoassay method according to claim 1, wherein the amine to be quantified is a monoamine derived from an amino acid.

7. An immunoassay method according to claim 3, wherein the monoamine is histamine.

8. An immunoassay of histamine according to claim 1, wherein the tracer is the compound:

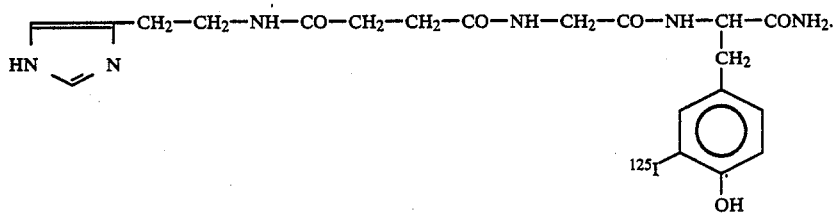

9. A kit for the immunoassay of a primary or secondary biological monoamine comprising ready for use reagents, namely:

an acylating reagent (I) of the formula:

NH₂COCH₂NH—CO—CH₂CH₂—CO—R′ in which R′ represents a leaving group selected from the group consisting of N-hydroxysuccinimide, halogen, —O—C—R″ and —S—R″, wherein R″ is a hydrocarbon radical or HO—C₆H₅—;

a tracer (II) of the formula:

X—NH—CO—R₁, wherein R₁ is a radical coupled to (1) an iodonated tyrosine or (2) an enzyme residue, and X is the residue of said monoamine;

and (III) an antibody raised against the tracer (II), said radical R₁ of said tracer (II) having been further selected so that said tracer (II) binds to said antibody (III) competively with respect to an acylated monoamine formed by the acylation of said monoamine by said acylating reagent (I).

10. A histamine immunoassay kit according to claim 9, wherein said reagent (I) is of the formula:

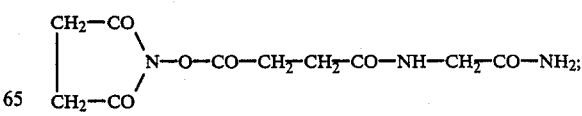

and said tracer (II) is of the formula: